United States Patent [19]
Magill

[11] Patent Number: 5,324,196
[45] Date of Patent: Jun. 28, 1994

[54] ORTHODONTIC APPLIANCE

[75] Inventor: Thomas S. Magill, New Hope, Minn.

[73] Assignee: Universal Dynamics, Inc., Minneapolis, Minn.

[21] Appl. No.: 62,776

[22] Filed: May 17, 1993

[51] Int. Cl.⁵ .............................................. A61C 3/00
[52] U.S. Cl. ........................................ 433/19; 433/6; 433/7
[58] Field of Search ............................... 433/6, 7, 19

[56] References Cited

U.S. PATENT DOCUMENTS

| | | | |
|---|---|---|---|
| 3,454,001 | 7/1969 | Stockfisch | 433/7 |
| 3,529,353 | 9/1970 | Schiaroli | 433/7 |
| 4,026,023 | 5/1977 | Fisher | 433/7 |
| 4,045,871 | 9/1977 | Nelson | 433/7 |
| 4,197,644 | 4/1980 | Ackerman, Jr. | 433/7 |
| 4,239,487 | 12/1980 | Murdock | 433/7 |
| 4,347,054 | 8/1982 | Kraus et al. | 433/7 |
| 4,431,411 | 2/1984 | Witzig | 433/6 |
| 4,433,956 | 2/1984 | Witzig | 433/7 |
| 4,482,318 | 11/1984 | Forster | 433/7 |
| 4,573,914 | 3/1986 | Nord | 433/18 |
| 4,597,738 | 1/1986 | Sander et al. | 433/19 |
| 4,619,609 | 10/1986 | Clark | 433/6 |

Primary Examiner—John J. Wilson
Attorney, Agent, or Firm—Leone & Moffa

[57] ABSTRACT

An orthodontic apparatus for treating skeletally based dental malocclusions. The orthodontic apparatus includes cooperating upper and lower surface apparatus for causing a mandibular displacement in a desired direction during an act of biting. An adjustment apparatus sets a relative position of the cooperating upper and lower surfaces.

18 Claims, 6 Drawing Sheets

5,324,196

ORTHODONTIC APPLIANCE

This invention relates to an apparatus for overcoming a skeletally based dental malocclusion, and more particularly to a formative orthodontic appliance that provides an adjustment system for an upper and lower bite block which cooperate to correct such a malocclusion.

BACKGROUND OF THE INVENTION

A malocclusion is a condition where teeth exist in a certain relationship varying from an ideal. A Class 2 malocclusion describes malocclusions that are skeletally as well as dentally based. In a Class 2 malocclusion, various bones, including those of the cranial base, cause positioning of the teeth resulting in a Class 2 molar relationship. In a Class 2 molar relationship, a maxillary first molar lies either directly over or in front of a mandibular first molar. This is in contrast to a "normal" or "ideal" occlusion wherein the maxillary first molar lies slightly behind the mandibular first molar.

Prior art provides a number of devices for the correction of malocclusions. For example, the prior art has used face bows. Face bows are wire springs attached to an appliance in the mouth to provide correcting force to the appliance. Elastic traction is provided by an elastic or retractable member attached to the head or the neck by strap or cap. The limitations of this approach are well known in the art.

An alternative method also well known in the art is a method of using bite blocks to provide restoring force for correcting the malocclusion. FIG. 1 shows an example of the bite blocks of the prior art as disclosed in U.S. Pat. No. 4,619,609 to Clark, issued Oct. 28, 1986. FIG. 1 shows upper and lower bite blocks 17, 21 with a wire retaining mechanism. The prior art provides a means for attachment of an inner bow 10 to an upper dental arch. This attachment means comprises a molded palate plate (not shown) having wire retainers (not shown) for connection of the palate plate to the upper teeth. The wire retainers receive and retain free ends of the inner bow 10, thereby accomplishing positioning of the bow. The palate plate incorporates a bite block 17 at the posterior side. The upper bite block 17 has a rearward and downward angled surface 18. The upper bite block 17 is positioned over the occlusal surfaces of the upper buccal teeth. A lower dental arch (not shown) conforms to the inner profile of the teeth of the central lower dental arch. Molded into the lower dental arch are spring fixing wires, for attachment to the mandibular teeth, as well as rearwardly directed wire hooks 19, for attachment of an elastic traction member 20. The bite blocks 17, 21 act to promote mandibular displacement between the upper and lower dental arches.

Prior art orthodontic appliances used to treat Class 2 malocclusions are designed to correct a malocclusion specific to a patient at a specific time of treatment. As the malocclusion changes over a period of time, the prior art appliance becomes obsolete. Since prior art devices are not adjustable for treatment of such skeletally based malocclusions, the present state of the art requires that new appliances be created and applied during the progression of a given patient's treatment. This necessity of creating multiple appliances precipitates less sensitive and less effective treatment, and contributes to higher costs for orthodontic treatment.

It is therefore the motive of the invention to provide, for treatment of Class 2 malocclusions, an orthodontic appliance that may be adjusted as treatment progresses.

SUMMARY OF THE INVENTION

The invention provides an orthodontic appliance wherein the relationship between cooperating angled surfaces of upper and lower bite blocks may be easily and accurately adjusted. The invention comprises an adjustable upper bite block and a lower bite block. Each adjustable bite block includes an angled surface and a drive tube mechanism. One side of the drive tube mechanism is molded within the palate plate. The apparatus of the invention provides a drive tube for extending or retracting the bite block for precise setting of the adjustable bite block. The position of the biting surface may easily be adjusted by an orthodontist.

It is one object of the invention to provide an adjustable orthodontic appliance for the correction of skeletally based dental malocclusions.

It is yet another object of the invention to provide a drive mechanism that affords precise setting of the apparatus to allow for increased effectiveness of treatment for skeletally based dental malocclusions.

It is yet a further object of the invention to provide for treatment of skeletally based dental malocclusions, an adjustable orthodontic appliance which allows for quick and simple adjustment.

Other objects, features and advantages of the present invention will become apparent to those skilled in the art through the Description of the Preferred Embodiment, Claims, and Drawings herein wherein like numerals refer to like elements.

BRIEF DESCRIPTION OF THE DRAWINGS

To illustrate this invention, a preferred embodiment will be described herein with reference to the accompanying drawings. The preferred embodiment concerns an apparatus for an adjustable orthodontic appliance.

DETAILED DESCRIPTION OF THE PREFERRED EMBODIMENT

Figure 2:
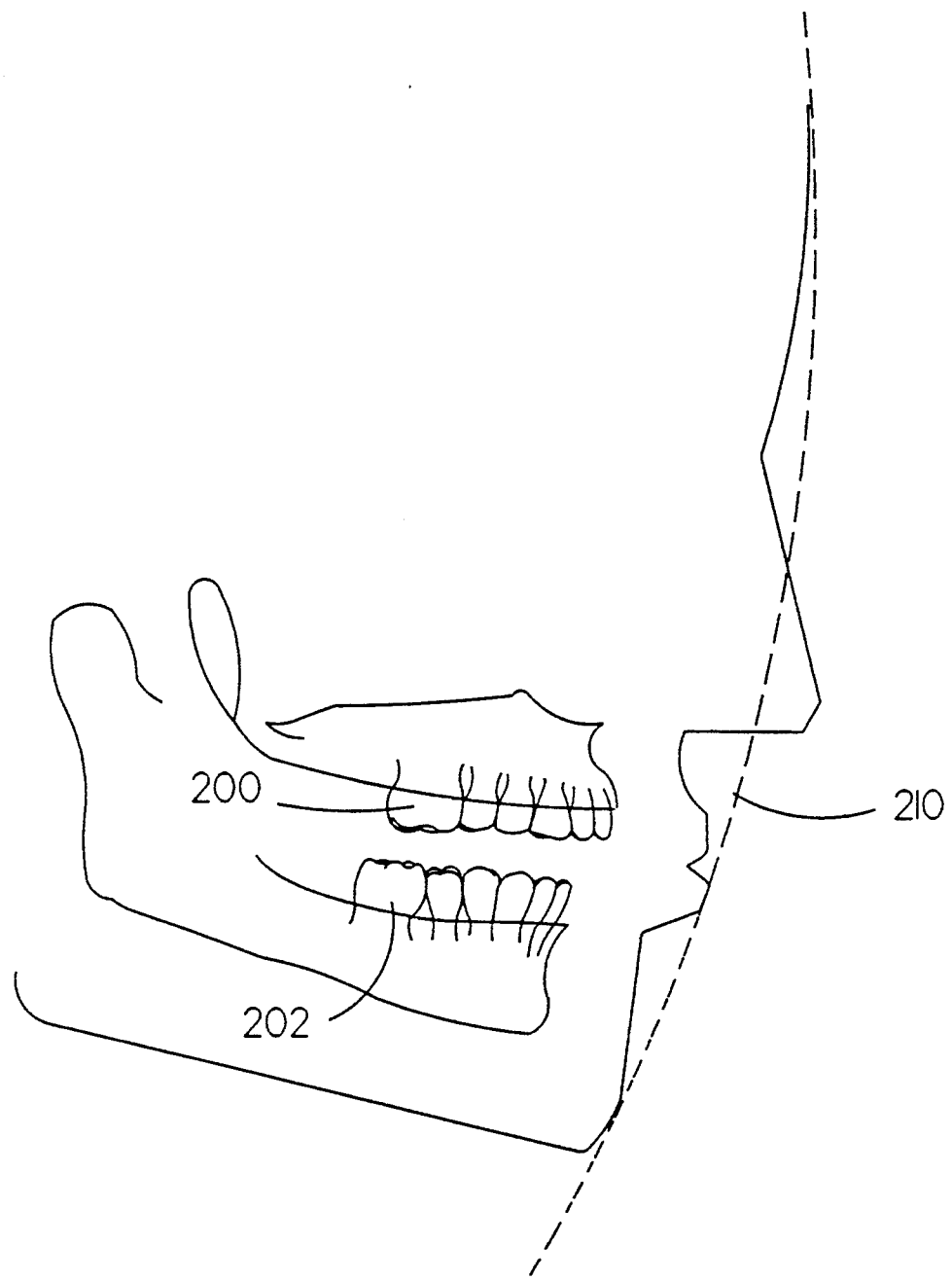
FIG. 2 shows an illustration of a Class 2 malocclusion of a type the apparatus of the invention may be used to correct.

Referring now to FIG. 2, FIG. 2 is an illustration of a Class 2 malocclusion of a type that the present invention is designed to correct. In a Class 2 malocclusion, the teeth of the upper jaw protrude relatively to the teeth of the lower jaw. A Class 2 malocclusion describes a position of the maxillary and mandibular first molar that is skeletally as well as dentally based. This type of malocclusion involves a "Class 2 molar relationship." A Class 2 molar relationship defines the condition where the maxillary first molar 200 lies over or in front of the mandibular first molar 202, rather than slightly behind the mandibular first molar 202 as in the normal molar relationship. The retrognathic profile associated with this condition is shown by profile 210, demonstrating the usual convex profile with the lower lip and chin positioned behind the upper lip.

Figure 3:
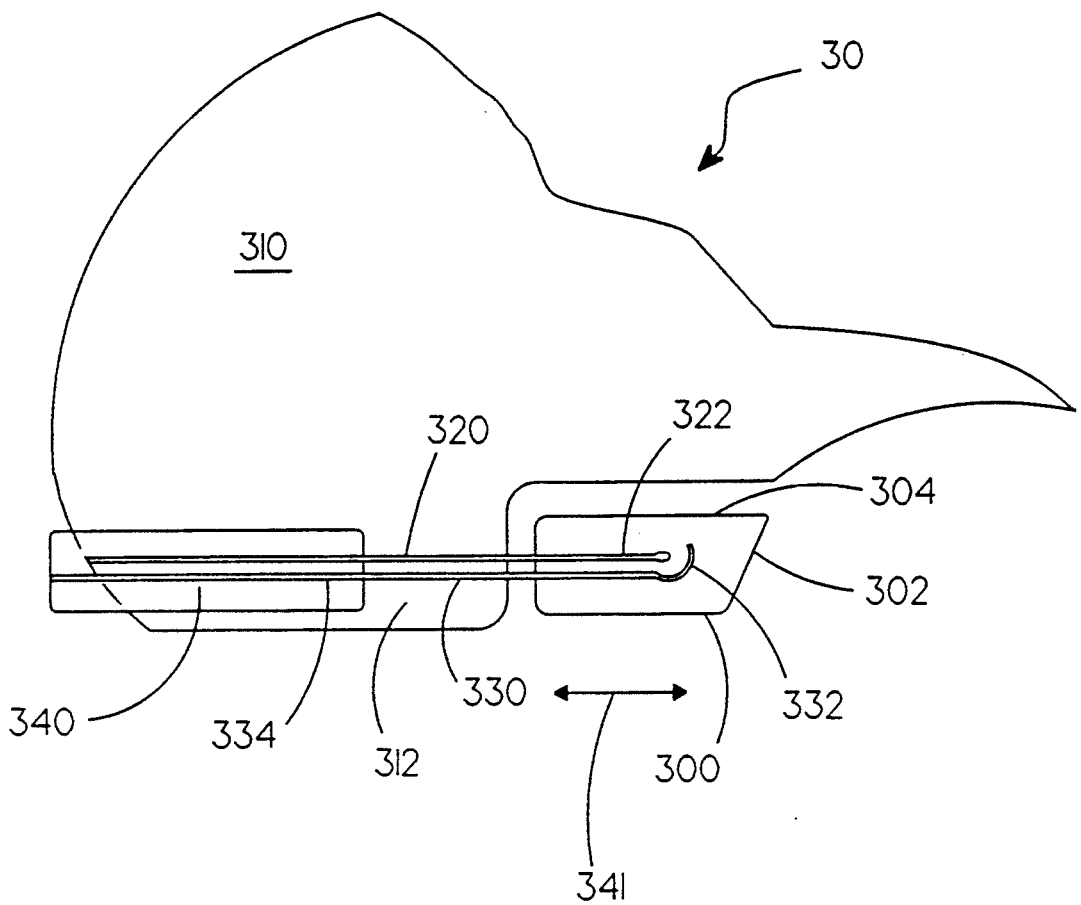
FIG. 3 shows a side view of a portion of the adjustable elements in one example of the apparatus of the invention.

Now referring to FIG. 3, FIG. 3 is a partial cross sectional side view showing one preferred embodiment of the adjustable elements of the invention. FIG. 3 demonstrates the adjustment capabilities of orthodontic appliance 30. The invention has an upper palate plate 310, worn within the mouth of the patient, and attached by conventional wire retaining means (not shown) to the upper teeth. The shown section of palate plate 310 comprises an integrated, molded palate plate bite block 312. The molded palate plate bite block 312 may be advantageously fashioned so as to rest over the occlusal surface of the maxillary first molar. The shown section of the invention also has an adjustable bite block 300, with an angled pressure surface 302.

Two stainless steel wire connectors 320 and 330 attach the adjustable bite block 300 to the molded palate plate bite block 312. The first wire connector 320 slideably attaches the adjustable bite block 300 to the molded palate plate bite block 312. The first wire connector 320 is fashioned in the form of a U-shaped loop 322. The U-shaped loop 322 may be advantageously anchored within the adjustable bite block 300. The two ends of the first wire connector 320 may advantageously pass from the adjustable bite block 300 into the molded palate plate bite block 312 in a generally parallel fashion. The parallel ends of the first wire connector 320 are mounted so as to slide laterally within the molded palate plate bite block 312, and to restrict motion of the adjustable bite block 300 in any other direction.

The second wire connector 330 provides the means of extending and retracting the adjustable bite block 300 in cooperation with a drive tube 340. One end of the second wire connector 330 may advantageously form a hooked end 332 which anchors the second wire connector 330 within the adjustable bite block 300. The hooked end 332 may advantageously pass over and around the U-shaped loop 322 of the first wire connector 320. The other end of the second wire connector 330 may be constructed as a threaded end 334. The threaded end 334 of the second wire connector 330 is threaded into the drive tube 340.

The drive tube 340 may advantageously be embedded within the molded palate plate bite block 312 of palate plate 310. Manipulating the drive tube 340 provides motive force in the directions indicated by double-headed arrow 341. The second wire connector 330 is moved laterally by rotational movement of the drive tube. In this way, movement of the second wire connector 330 provides for the extension and retraction of the attached adjustable bite block 300. The positioning of the adjustable bite block 300 is thus accomplished through adjustment of the drive tube 340.

The adjustable bite block 300 also has an upper pressure surface 304. When the adjustable bite block 300 is inserted into the mouth of the patient, the upper pressure surface 304 rests on the occlusal surface of the upper buccal teeth, providing support for the adjustable bite block 300 in the vertical plane of the mouth.

Figure 1:
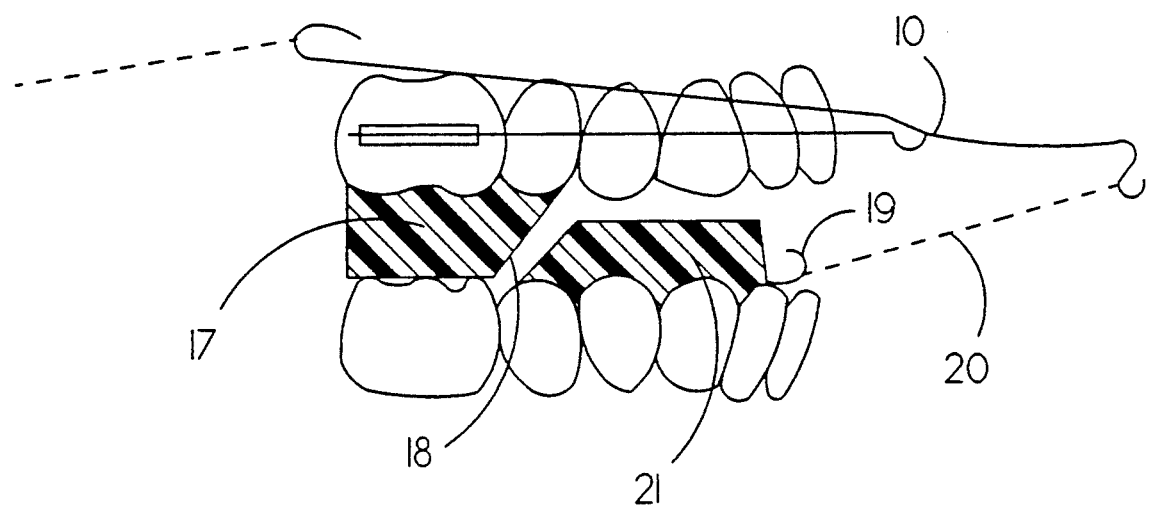
FIG. 1 shows a side view of a prior art bite block orthodontic apparatus.

The angled pressure surface 302 slopes downward and towards the rear of the mouth. The angled pressure surface 302 acts in cooperation with an opposing angled surface of a lower bite block, similar to surface 18 shown in FIG. 1, during a biting motion. The biting motion produces a forward mandibular displacement that operates to correct Class 2 malocclusions.

Drive tube 340 provides an adjustment means that is used to position the angled pressure surface 302 for increased effectiveness through the progression of treatment. Other means of adjusting the adjustable bite block 300 are possible, as will be recognized by those skilled in the art having the benefit of this disclosure.

Figure 4:
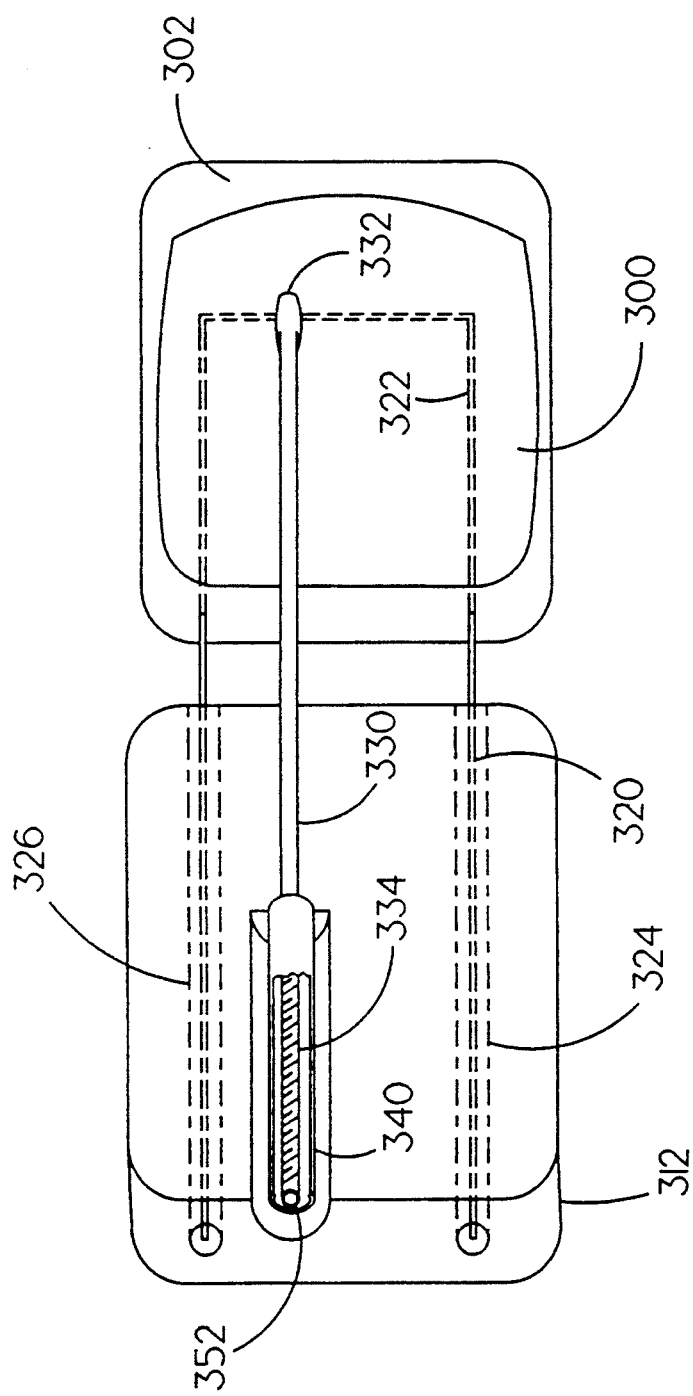
FIG. 4 shows a top view of one example of the adjustment elements of the apparatus of the invention.

FIG. 4 shows a top view of a portion of the preferred embodiment of the adjustment apparatus of the invention. This portion shows the adjustable means of the orthodontic apparatus and comprises the molded palate plate bite block 312, the adjustable bite block 300, and the angled pressure surface 302.

FIG. 4 shows in greater detail the means by which the position of the adjustable bite block 300 may be adjusted. The first wire connector 320 provides a means of slideably attaching the adjustable bite block 300 to the molded palate plate bite block 312. The first wire connector 320 has a U- 0 shaped loop 322 embedded within the adjustable bite block 300, and two ends passing into the molded palate plate bite block 312. The two ends of the first wire connector 320 slide within a pair of cylinders 324 and 326 that are molded into the molded palate plate bite block 312 so as to allow adjustment of the adjustable bite block 300. As discussed hereinabove, the second wire connector 330 provides a means of extending and retracting the adjustable bite block 300. The hooked end 332 formed by the second wire connector 330 may be advantageously embedded in the adjustable bite block 300. The hooked end 332 passes over and partially around the U-shaped loop 322 of first wire connector 320, fixing the position of the second wire connector 330 within the bite block 300. The threaded end 334 of the second wire connector 330 passes from the adjustable bite block 300 into the drive tube 340 embedded within the molded palate plate bite block 312. The threaded end 334 of the second wire connector 330 is set within the drive tube 340.

In one embodiment of the invention, the position of the adjustable bite block 300 may be adjusted by inserting an allen wrench into opening 352 and rotating the drive tube 340. Rotation of the drive tube 340 is translated into lateral movement by the threaded end 334, extending and retracting the second wire connector 330, depending upon the rotational direction of the drive tube. The second wire connector 330 thus acts as a drive shaft and sets the position of the adjustable bite block 300.

Figure 5:
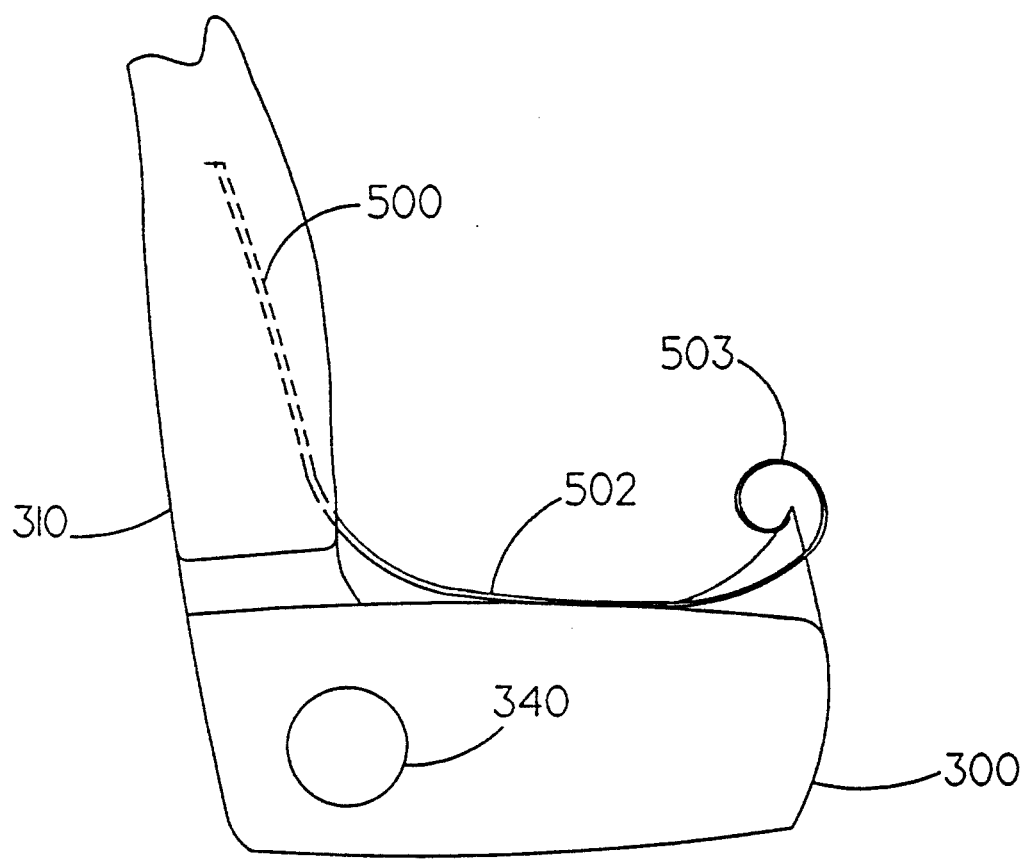
FIG. 5 shows a partial rear view of the apparatus of the invention, looking into a drive tube.

Now referring to FIG. 5, FIG. 5 shows a partial rear view of the apparatus of the invention, looking into the drive tube. The palate plate 310 includes a wire retainer 502. The wire retainer 502 has an embedded end 500 within the palate plate 310. An exterior portion of the wire retainer 503 provides the means for attaching the palate plate 310 to the upper teeth in a manner familiar to those skilled in the art. Those skilled in the art will recognize that a plurality of such wire retainers may be employed in order to maintain the placement of the appliance within a patient's mouth. The palate plate 310, when placed within the mouth of the patient, lies over the upper dental arch.

Figure 6:
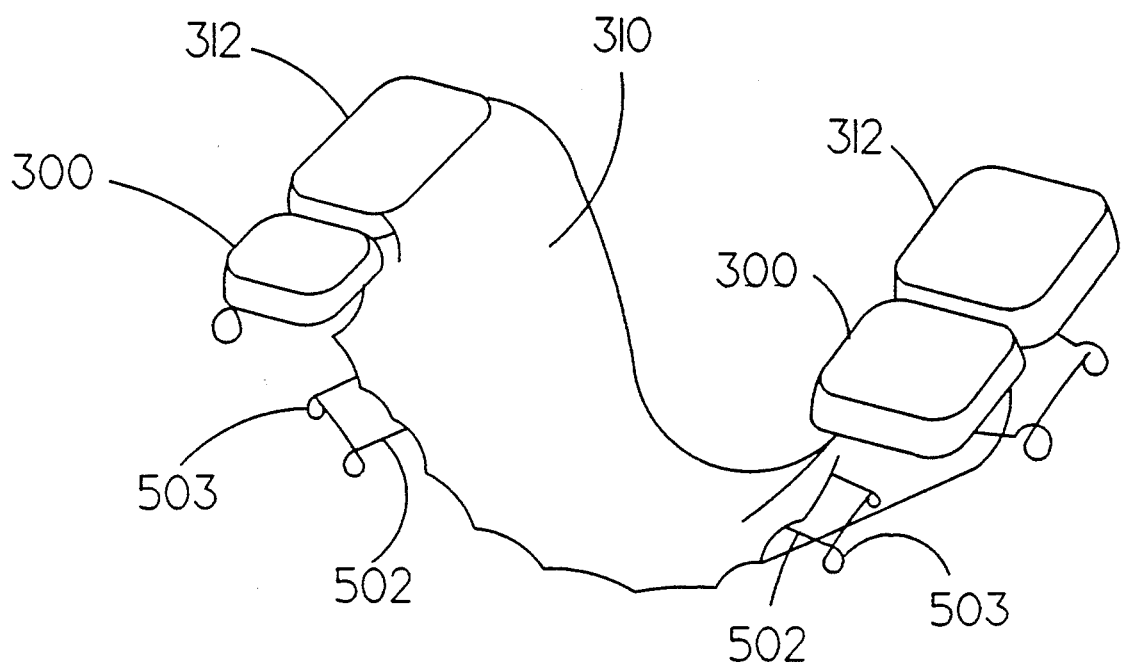
FIG. 6 shows a three dimensional perspective of the apparatus of the invention.

Referring now to FIG. 6, FIG. 6 shows a three dimensional perspective view of the apparatus of the invention. FIG. 6 illustrates a perspective showing the occlusal side of the apparatus of the invention. The apparatus of the invention has a palate plate 310, with a pair of molded palate plate bite blocks 312. The molded palate plate bite blocks 312 are connected to a corresponding pair of adjustable bite blocks 300. The adjustable bite blocks 300 each incorporate an angled pressure surface 302. The angled pressure surfaces 302 work in cooperation with opposing angled surfaces of lower bite blocks. This operates to correct malocclusions as described hereinabove. The palate plate 310 also has wire retainers 502 that attach palate plate 310 to the upper teeth.

The invention has been described herein in considerable detail in order to comply with the Patent Statutes and to provide those skilled in the art with the information needed to apply the novel principles and to construct and use such specialized components as are required. However, it is to be understood that the invention may be carried out by specifically different equipment and devices, and that various modifications, both as to the equipment details and operating procedures, may be accomplished without departing from the scope of the invention itself.

What is claimed is:

1. An orthodontic apparatus for treating skeletally based dental malocclusions, the orthodontic apparatus comprising:
   (a) upper palate plate means having an adjustable block mount and a moveable bite block slideably attached to the adjustable block mount;
   (b) lower plate means having a lower bite block wherein the lower bite block has a first surface; and
   (c) adjustment means, affixed to the upper palate plate, for positioning said moveable bit block, the moveable bite block having a second surface the second surface being positioned and arranged to contact the first surface so as to provide a malocclusion correction force.

2. The orthodontic apparatus of claim 1 further comprising a retainer means partially embedded within the upper palate plate means.

3. The orthodontic apparatus of claim 2 wherein the first surface and second surface cooperate during biting so as to treat Class 2 malocclusions.

4. The orthodontic apparatus of claim 3 wherein the adjustment means further comprises:
   (a) a drive tube apparatus embedded within the upper palate plate means; and
   (b) a drive shaft means having a threaded end embedded within the drive tube apparatus and an anchored end embedded within the moveable bite block.

5. The orthodontic apparatus of claim 1 wherein the first surface and second surface cooperate during biting so as to treat Class 2 malocclusions.

6. The orthodontic apparatus of claim 1 wherein the adjustment means further comprises:
   (a) a drive tube apparatus embedded within the upper palate plate means; and
   (b) a drive shaft means having a threaded end within the drive tube and an anchored end within the moveable bite block.

7. The orthodontic apparatus of claim 1 wherein the moveable bite block has an upper pressure surface for providing a contact point for additional support and force for mandibular displacement.

8. The orthodontic apparatus of claim 1 wherein the moveable bite block contacts the mouth to provide support in the vertical plane of the mouth.

9. The orthodontic apparatus of claim 1 wherein the adjustment means further comprises a wire connector having a first end embedded in the moveable bite block and a cylinder embedded in the upper palate plate for slideably receiving a second end of the wire connector.

10. An adjustable orthodontic apparatus for treatment of a malocclusion, comprising:
    (a) upper palate plate means conformed to fit within a patient's mouth, the upper palate plate means comprising a first bite block conformed to be positioned over an occlusal surface of a maxillary first molar;
    (b) a retainer means for securing attachment of the upper palate plate means, the retainer means being affixed to the upper palate plate means;
    (c) a moveable bite block comprising a first surface;
    (d) a lower plate having a lower bite block comprising a second surface positioned so as to oppose and cooperate with the first surface so as to produce a mandibular displacement;
    (e) a connecting and stabilizing means, connected between the first bite block and the moveable bite block, for slideably connecting the moveable bite block to the first bite block and stabilizing a position of the moveable bite block; and
    (f) an adjustment means for moving and fixing a position of the moveable bite block relative to the first bite block, the adjustment means having a first adjustment element affixed to the first bite block and a second adjustment element affixed to the moveable bite block.

11. The adjustable orthodontic apparatus of claim 10 wherein the retainer means comprises a plurality of wire retainer means partially embedded within the palate plate means.

12. The adjustable orthodontic apparatus of claim 11 wherein the first surface and the second surface cooperate as to treat Class 2 malocclusions.

13. The adjustable orthodontic apparatus of claim 12 wherein the adjustment means comprises:
    (a) a drive tube apparatus embedded within the first bite block; and
    (b) a drive shaft means having a threaded end within the drive tube and an anchored end within the moveable bite block.

14. The adjustable orthodontic apparatus of claim 13 wherein the connecting and stabilizing means comprises a wire connector means looped through the moveable bite block the wire connector means having two parallel ends that slideably engage the moveable bite block to the first bite block, thereby allowing the moveable bite block to be extended and retracted, 15. The adjustable orthodontic apparatus of claim 10 wherein the first surface and the second surface cooperate so as to treat Class 2 malocclusions.

16. The adjustable orthodontic apparatus of claim 16 wherein the adjustment means comprises:
    (a) a drive tube apparatus embedded within the first bite block; and
    (b) a drive shaft means having a threaded end within the drive tube and an anchored end within the moveable bite block.

17. The adjustable orthodontic apparatus of claim 10 wherein the connecting and stabilizing means comprises a wire connector means looped through the moveable bite block, the wire connector means having two parallel ends that slideably engage the moveable bite block to the first bite block, thereby allowing the moveable bite block to be extended and retracted.

18. The orthodontic apparatus of claim 10 wherein the connecting and stabilizing means further comprises a wire connector having a first end embedded in the moveable bite block and a cylinder embedded in the first bite block plate for slideably receiving a second end of the wire connector.

* * * * *

UNITED STATES PATENT AND TRADEMARK OFFICE
CERTIFICATE OF CORRECTION

PATENT NO. : 5,324,196
DATED : June 28, 1994
INVENTOR(S) : Thomas S. Magill

It is certified that error appears in the above-indentified patent and that said Letters Patent is hereby corrected as shown below:

Column 4, line 20, delete the phrase "U-O"and replace it with --U- --.

Column 5, line 31, delete the word "bit" and replace it with --bite --.

Column 6, line 32, delete the phrase "as to " and replace it with -- so as to --.

Column 6, line 43, delete the word "block" and replace it with --block, --.

Column 6, line 45, delete the word "retracted,"and replace it with -- retracted. --.

Column 6, line 49, delete the number "16" and replace it with --15 --.

Signed and Sealed this

Sixth Day of June, 1995

Attest:

BRUCE LEHMAN

Attesting Officer

Commissioner of Patents and Trademarks